United States Patent [19]
Beach

[11] Patent Number: 5,951,476
[45] Date of Patent: Sep. 14, 1999

[54] METHOD FOR DETECTING BRAIN MICROHEMORRHAGE

[76] Inventor: Kirk Watson Beach, 4023 Meridian Ave. North, Seattle, Wash. 98103

[21] Appl. No.: 08/970,972

[22] Filed: Nov. 14, 1997

[51] Int. Cl.$^6$ ........................................................ A61B 8/08
[52] U.S. Cl. ........................... 600/437; 600/448; 600/451; 600/453; 600/455
[58] Field of Search .................................... 600/437, 448, 600/451, 453, 455

[56] References Cited

U.S. PATENT DOCUMENTS

| | | | |
|---|---|---|---|
| 3,713,329 | 1/1973 | Munger | 73/67.9 |
| 5,088,498 | 2/1992 | Beach et al. | 128/661.07 |
| 5,183,046 | 2/1993 | Beach et al. | 128/661.07 |
| 5,289,820 | 3/1994 | Beach et al. | 128/661.07 |
| 5,379,770 | 1/1995 | Van Veen | 128/661.07 |
| 5,573,012 | 11/1996 | McEwan | 128/782 |

Primary Examiner—Scott M. Getzow
Assistant Examiner—Eleni Mantis Mercader
Attorney, Agent, or Firm—Robert W. Beach

[57] ABSTRACT

Continued bleeding into a pocket or hematoma in the cranium could exert pressure on the brain which would move it relative to the cranium to force the brain stem into the medulla oblongata to arrest breathing. Such brain micromovement is detected by projecting bursts of ultrasound into one or both of the temple areas of the cranium or into the medulla oblongata, and the readout of echoes received from different depths is displayed on a screen. The readout of the echoes indicates continued microshifts of the brain relative to the cranium. To differentiate microshifts of the brain relative to the cranium caused by continued intracranial bleeding as distinguished from pulsations of the brain relative to the cranium caused by supply of blood to the brain from the heart and return of blood from the brain to the heart, the timing of the bursts of ultrasound into the cranium is synchronized with the pulse indicated by a heart pulse monitor.

11 Claims, 4 Drawing Sheets

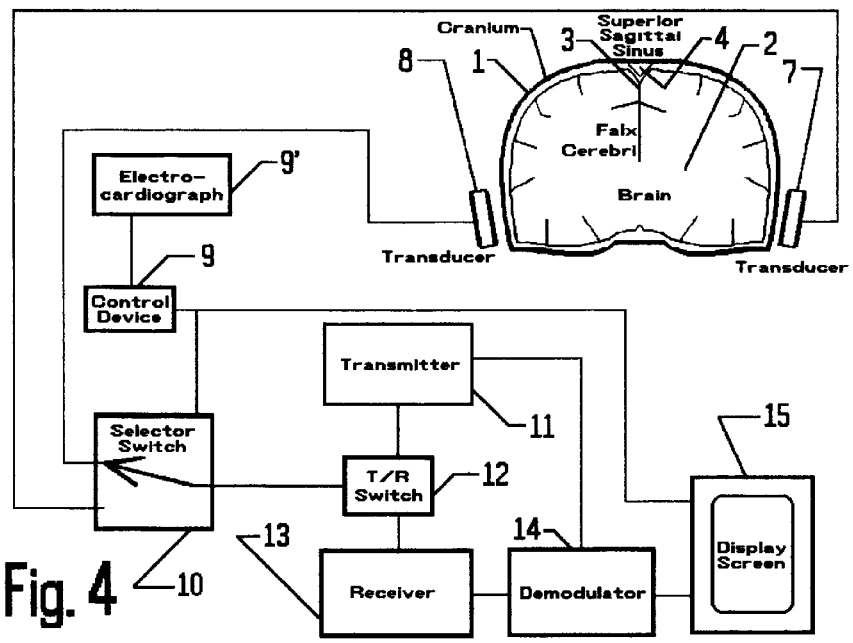
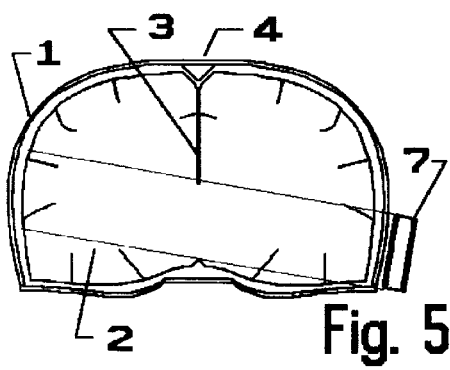
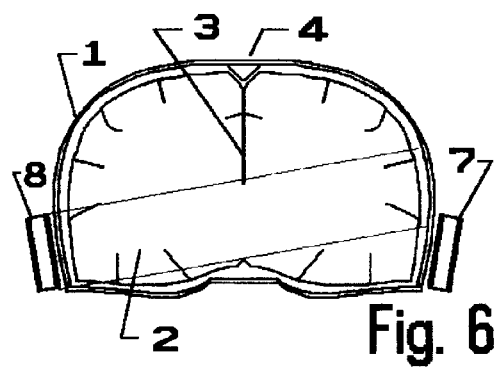

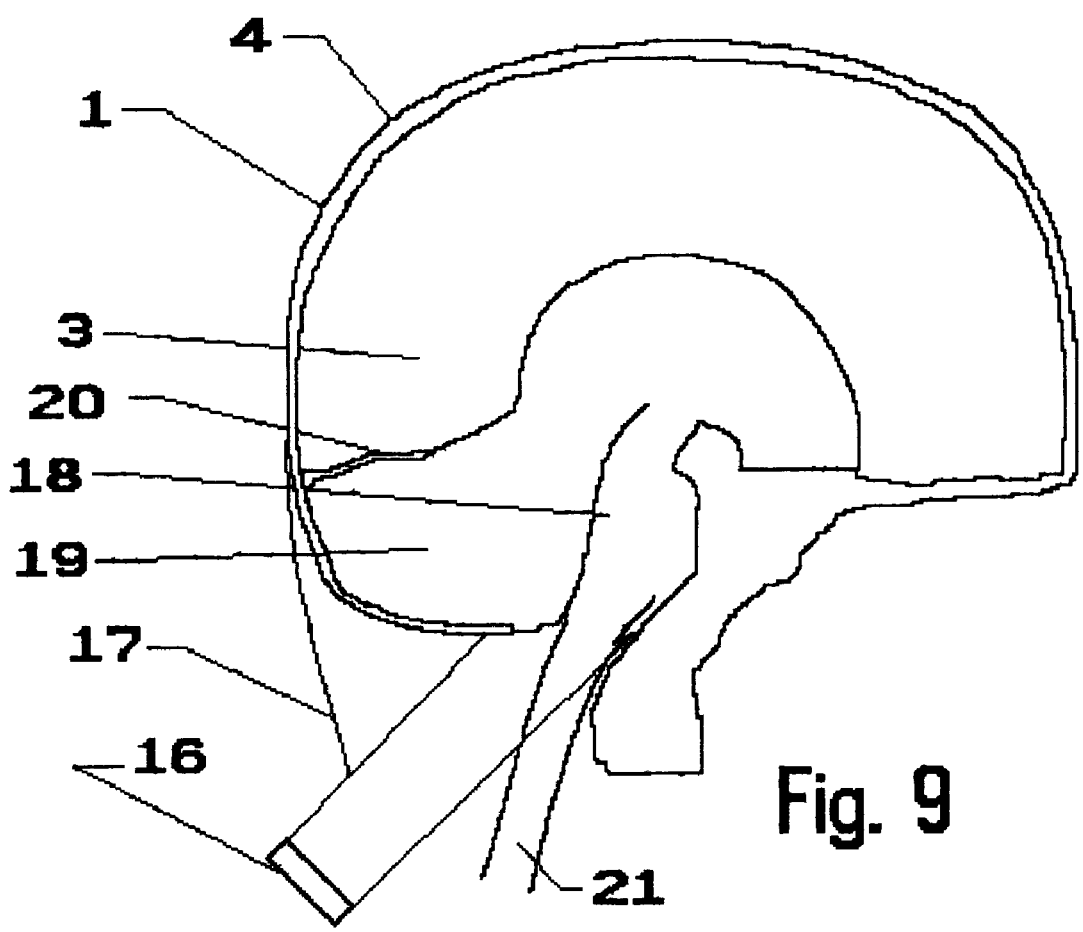

METHOD FOR DETECTING BRAIN MICROHEMORRHAGE

BACKGROUND OF THE INVENTION

1. Field of the Invention

This invention relates to a method for detecting intracranial microbleeding by continuing microshifting of a person's brain within the cranium.

2. The Problem

Head trauma which appears to be minor, that is an injury resulting from an impact to the skull, such as by a blow or a fall or in a motorcycle accident, may have serious or even fatal consequences. If the skull impact is sufficiently severe to cause a brain concussion resulting in at least temporary and transient brain malfunction, the patient would be held in a hospital probably for several days for testing and observation. On the other hand, if the trauma appears to be minor and visual examination in the emergency room of a hospital does not reveal any problem or cause for concern, the patient will probably be discharged within an hour or two.

It is possible that the trauma may have displaced the cranium relative to the brain, particularly sideways, sufficiently to rupture one or more small veins, the bleeding from which would normally be undetected by the usual emergency room visual examination. If the patient is sent home, continued bleeding can cause an accumulation of blood in a pocket or hematoma at one side of the brain which initially would shift the brain to an eccentric position in the cranium. If the bleeding continued to a sufficient extent and for a sufficient period of time, the pressure of the accumulated blood against the brain could cause drowsiness or even cause the patient to fall into a coma.

The medulla oblongata forming the lower portion of the brain passes through the foramen magnum, which is the large opening in the occipital bone that forms the posterior part of the skull, to become the spinal cord. The brain is readily deformable and continued pressure on it by the progressive accumulation of blood in an intracranial hematoma could force the medulla oblongata farther into the foramen magnum. The medulla oblongata is tapered downwardly and contains the respiratory center which controls breathing. The continued pressure on the brain may wedge the medulla oblongata into the foramen magnum, causing sufficient pressure on it to result in respiratory arrest, usually while the patient is unconscious, and consequent death within about twenty-four hours after the injury.

Prior Art

If medical personnel were alerted to the abnormal shift of the brain relative to the cranium caused by the accumulation of blood in a pocket at one side of the cranium, diagnosis could be effected by taking a computer assisted tomography (CAT) picture of the head, but such a CAT scan probably would not disclose a microshift of the brain but only a substantial shift effected by continued bleeding into the cranial pocket for several hours. Such a diagnosis could be effected in a hospital if the patient remained for a sufficient period of time After proper diagnosis, the blood accumulation condition could be remedied by a surgeon cutting an aperture in the skull (trephination) at the location of the hematoma and installing a drain to allow blood to flow out of the pocket in the skull, thereby relieving pressure against the brain and allowing it to resume its proper position within the cranium. When the pressure on the brain is relieved by draining blood, the patient rouses. Such surgical procedure would be followed, however, only on the basis of an appropriate diagnosis.

Basic Problem

The basic problem, therefore, is to determine when a patient might be at risk of having a continuing brain displacement relative to the cranium which would dictate that the patient remain in the hospital for a day or two for evaluation and examination. The normal procedure, as mentioned above, would be to release the patient from the emergency room in an hour or two, during which time there normally would be no evidence of the brain being shifted relative to the cranium by pressure of blood accumulated in a pocket.

It has been determined that, when blood escapes from a ruptured blood vessel or blood vessels in the skull, such blood may accumulate slowly in a pocket and effect pressure against the brain which would cause it to move sideways away from the side of the cranium where the pocket is formed. Such brain shift would be very slow, such as for a distance of perhaps one centimeter in ten hours, or about one millimeter per hour, or seventeen microns per minute. If such minute shifting could be detected, it would forewarn medical personnel that a problem of substantial brain shift could occur over a period of several hours, so that it would be desirable to retain such a patient in the hospital for observation and tests for at least a day.

The basic problem, therefore, is to be able to detect an early continuing microshift of the brain relative to the cranium caused by increasing pressure of blood in a pocket or hematoma resulting from slight continuing cranial bleeding.

Use of Above Prior Art

As stated above, the usual prior art procedure for detecting brain shift relative to the cranium has been the taking of a CAT scan picture or pictures of the skull, but such CAT scan pictures do not reliably identify a very small displacement or microshift of the brain relative to the cranium.

A standard diagnostic workup includes expensive neuroimaging, i.e. CAT scan imaging or magnetic resonance imaging. Such neuroimaging may not show any shift of the brain relative to the cranium within the first hour after injury and may not detect a small blood pocket or hematoma.

SUMMARY OF THE INVENTION

A principal object of the present invention is to detect a continuing microshift of the brain relative to the cranium by pressure caused by progressive accumulation of blood in a pocket in the cranium resulting from a ruptured blood vessel or blood vessels.

A further object is to detect such a continuing microshift of the brain reliably, quickly and comparatively inexpensively.

Another object of the invention is to utilize apparatus for detecting such a continuing microshift of the brain which is effective and easy to use.

Such objects can be accomplished by ultrasonographic apparatus including at least one transcranial ultrasound transducer applied to the skull, such as located over the right temple, the left temple or the foramen magnum, for transmitting bursts of high frequency ultrasound pulses into the head through the cranium and receiving ultrasound echo signals from brain.

Additional Prior Art

The application of ultrasonic pulses to the head is not new, such technique being described, for example, in U.S. Pat. No. 5,379,770, issued Jan. 10, 1995, for Method and Apparatus for Transcranial Doppler Sonography for ascertaining velocity of blood flow at a position within the head of a subject but, as far as known, ultrasonography has not been used for the purpose of obtaining information relative to continuing microshifting of the brain within the cranium caused by progressive accumulation of blood in a pocket or hematoma.

A reference book entitled *Biomedical Ultrasonics*, by P. N. T. Wells, Academic Press, London, New York and San Francisco, 1977, describes the application of ultrasonic pulse echo methods utilized in neurology in Section 6.16e on pages 316 to 324. The use of echoencephalography is discussed to locate the midline of the brain. This publication states near the bottom of page 317 that:

> There is quite a wide divergence between various authors in estimating the accuracy with which the midline can be localized. Readouts are displayed on page 318, stating:
>
> (c) Scans of a patient with brain midline structures displaced by six millimeters toward the left side by an entrocerebral hemorrhage on the right side. The time markers on the scans of the normal patient correspond to ten millimeter distances in soft tissues. At the middle of page 319 it is stated:
>
> The first single echo or the first of two echoes which are separated by no more than four millimeters that has an amplitude above a fixed threshold and which lies within the middle gate is accepted as an echo from a midline structure. Thus the echoes having the greatest amplitude are interpreted as originating from the midline tissue of the brain.
>
> Near the bottom of page 321 it is stated:
>
> The identification of echoes arising from within the skull is at best difficult. Great skill and clinical acumen are necessary if reliable results are to be obtained. The present invention is not concerned with the location of the brain midline.

Ultrasonic apparatus generally of the type that can be used in the method of the present invention is disclosed in Beach et al. U.S. Pat. No. 5,088,498, issued Feb. 18, 1992, for Ultrasonic Plethysmograph, and in continuation patents No. 5,183,046 and No. 5,289,820.

BRIEF DESCRIPTION OF THE DRAWINGS

FIG. 4 is a vertical transverse midsection through the upper portion of a head with transducers of brain velocimeter ultrasonic apparatus applied to both of its temporal regions, respectively, which apparatus is shown diagrammatically including a block circuit diagram;

FIG. 5 is a vertical transverse midsection through the upper portion of the head with transducers of brain velocimeter ultrasonic apparatus applied to both of its temporal regions, respectively, one of such transducers indicated as being activated in one phase;

FIG. 6 is a vertical transverse midsection through the upper portion of the head with transducers of brain velocimeter ultrasonic apparatus applied to both of its temporal regions, respectively, the other of such transducers being indicated as being activated in one phase;

FIG. 9 is a vertical longitudinal midsection through the head with a transducer of brain velocimeter ultrasonic apparatus aimed at the medulla oblongata.

DETAILED DESCRIPTION

Figure 1:
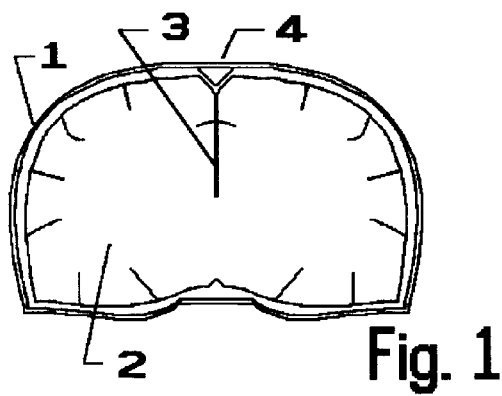
FIG. 1 is a vertical transverse midsection through the upper portion of the head showing the brain in normal position within the cranium.

The vertical transverse midsection through the head of FIG. 1 shows the cranium 1 encasing the brain 2 under normal conditions in which the brain is centered within the cranium and the deep medial cleft between the left and right hemispheres of the brain, i.e., the falx cerebri 3, identifying the midline of the brain, extends vertically.

The brain is enclosed in three membranes within the cranium, the outermost membrane being the dura mater, the innermost membrane being the pia mater, and the intermediate membrane being the arachnoid. All of these membranes are highly vascular, that is, they contain many blood vessels. The venous sinus is a passage in the dura mater for flow of venous blood returning from the head to the heart. The superior sagittal sinus 4 extends fore and aft across the top of the brain.

Figure 2:
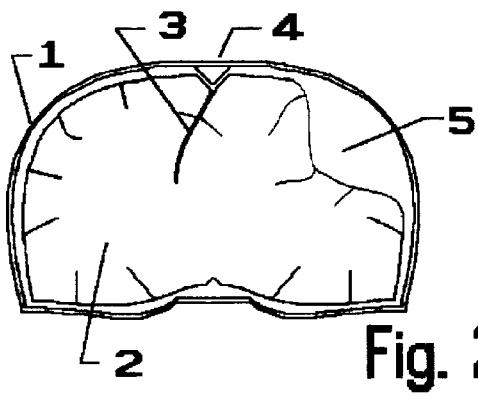
FIG. 2 is a vertical transverse midsection through the head showing an advanced subdural hematoma.

A sharp jolt to one side of the head by a blow or by a fall can cause the skull to move abruptly relative to the brain because of the inertia of the brain and cause rupture of veins in one or more of the membranes enveloping the brain. Blood from such ruptured veins can accumulate in a pocket 5 between the dura mater and the arachnoid brain-enveloping membranes, a subdural hematoma, as shown in FIG. 2, or between the membranes and the brain, forming an epidermal hematoma 6, shown in FIG. 5. Either type of hematoma may become increasingly distended over a considerable period of time by continued bleeding, such as for several hours, because the progress of the bleeding may be very slow.

Since the brain is substantially incompressible but readily deformable, continued pressure on the brain by a distending hematoma could displace the brain progressively laterally in the cranium and force the medulla oblongata farther into the foramen magnum, which is the large opening in the occipital bone at the base of the cranium through which the medulla oblongata passes from the brain to become the spinal cord. Since the medulla oblongata is tapered downwardly, such pressure on the brain could wedge the medulla oblongata into the foramen magnum with sufficient pressure to cause dysfunction of the respiratory center contained in the medulla oblongata and arrest breathing to cause death.

While aggravated deformation of the brain sufficient to cause dysfunction of the respiratory center would usually occur over a relatively long period of time, such as at least more than an hour, and usually as long as twenty-four hours, it would be highly desirable for medical personnel to be alerted to the abnormal progressive brain displacement relative to the cranium as soon as possible. The function of the present brain ultrasonic velocimeter apparatus is to detect abnormal continuing microshifts of the brain relative to the cranium within a matter of minutes after admission of the patient to the emergency room of a hospital, and to do it inexpensively. Such brain ultrasonic velocimeter apparatus is shown diagrammatically in FIG. 4 and includes one or more transducers 8 applied to the temples of the head 1 or to the foramen magnum.

The purpose of the velocimeter is to detect very small continuing abnormal very slow nonpulsatile movement of brain relative to the cranium caused by the exertion of continued pressure on the brain resulting from continuing bleeding into a cranium pocket or a hematoma. The brain also is moved normally slightly relative to the cranium by periodic swelling and contraction of the brain produced by the pulsating supply of blood to the brain and alternate draining of blood back to the heart effected by normal beating of the heart. To distinguish abnormal movement, shifting or displacement of brain relative to the cranium produced by continuing distention of a hematoma from the normal periodic pulsation movement of the brain relative to the cranium resulting from supply of blood by the heart and return of blood to the heart, it is desirable to take a reading of the brain velocity relative to the skull in synchronism with pulsation of the brain caused by inflow and outflow resulting from heart blood-pumping action. Consequently, the velocimeter action is coordinated with a heart pulse monitor 9'.

While a single transducer could be used, two transducers 7 and 8, one for each temple, are shown in FIG. 4 in the block diagram of the ultrasound velocimeter. Use of two transducers provides greater reliability and the ability to cross-check results. The ultrasonic generator is an ultrasonic Doppler or time domain phase displacement system with a phase or time domain demodulation and with readout display components. The apparatus is optimized to measure and display very slow velocities near one millimeter per hour or as slow as 0.30 mm. per hour because of the relatively low pulse repetition frequency (PRF)used, in contrast to conventional blood velocimeters which are only capable of detecting velocities within the range of one centimeter per second to five hundred centimeters per second.

The apparatus shown in FIG. 4 includes a control device 9 for timing ultrasonic bursts to a transmitting transducer in synchronism with heartbeats monitored by the electrocardiograph 9'. One or two or a very few ultrasonic bursts could be triggered by the control device 9 for each cardiac cycle. There is a short delay between bursts of 0.25 second to 2.0 seconds. A selector switch 10 directs the ultrasonic pulses automatically to the temple-applied transducers 7 and 8 alternately. The transducer is activated by the transmitter 11 to transmit a burst of ultrasonic pulses by way of the alternate transmit-receive (T-R) switch 12. Echoes from the transducers 7 and 8 are received and amplified by the receiver 13 from which the signals pass to the demodulator 14 that conditions and times the signals for readout display on the screen 15.

The transmitter 11 transmits ultrasound pulses at frequencies of 100 kilohertz (KHz) to 2 megahertz (MHz), depending upon the bone penetration of the apparatus desired. Bursts of ultrasound pulses having such frequencies can penetrate the bone in the temporal area of the cranium. FIG. 5 indicates a burst of pulses being transmitted through one temple of the cranium by one of the transducers 7, and FIG. 6 indicates a burst of ultrasound pulses being transmitted through the other temporal area of the cranium by the other transducer 8. Transmission of such ultrasonic pulse bursts is effected by shifting of the selector switch 10 to provide alternating phases of the velocimeter test. The ultrasonic pulses are reflected from brain tissue parenchyma to produce echoes.

Figure 7:
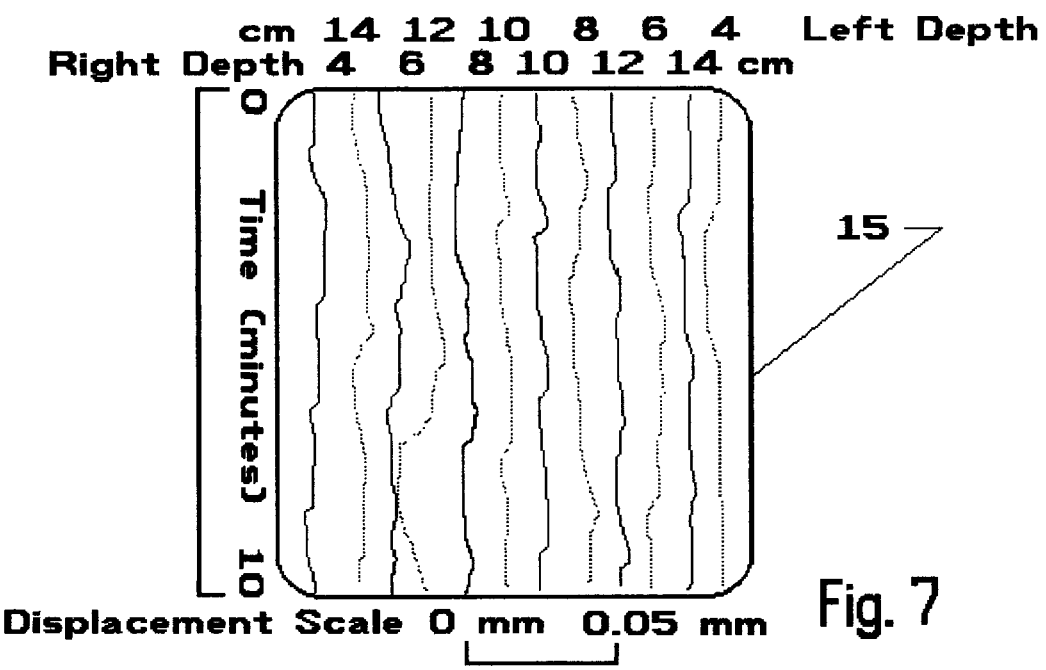
FIG. 7 is a diagrammatic representation of a brain velocimeter ultrasonic apparatus signal generated by the apparatus corresponding to a brain in unshifted condition relative to the cranium.
Figure 8:
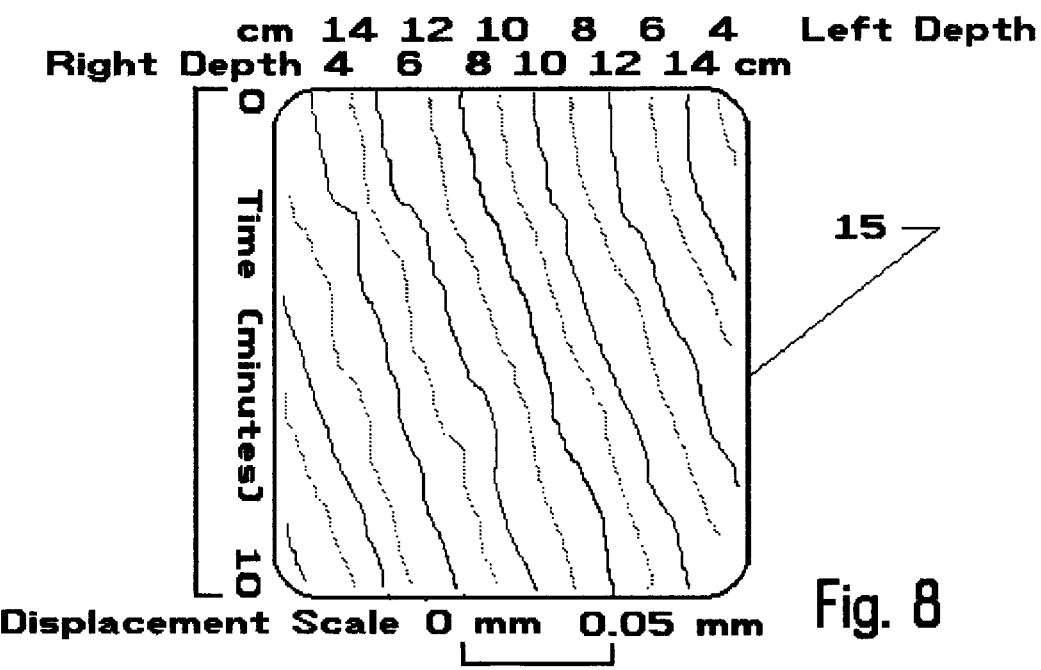
FIG. 8 is a diagrammatic representation of a brain velocimeter signal generated by the apparatus corresponding to a brain which has been progressively shifting a small amount from its normal position relative to the cranium.

The display resulting from reflected echoes of ultrasonic pulse bursts on screen 15 is illustrated in FIGS. 7 and 8. These FIGURES represent signals generated by echoes from ultrasonic pulse bursts transmitted from the right transducer 7 as solid lines, and represent signals generated by echoes from ultrasonic pulse bursts transmitted by the left transducer 8 as dotted lines. Each horizontal line or abscissa through the display represents the pattern of echoes produced by one ultrasound burst and received from brain parenchyma at four to thirty-two different depths within the brain in accordance with the operation of the demodulator 14. The number of depths corresponds to the number of upright lines in the readout display, six depths being represented by the six solid lines and six depths being represented by the six broken lines in FIGS. 7 and 8. The ordinates of these displays indicate the shifts of the echo patterns and consequently of the brain over a period of time of a few minutes, such as ten minutes.

As designated in these FIGURES, the ordinates indicate that the graphs represent plotting of the echo representations over a period of time of ten minutes. The successively lower abscissae of these graphs represent the progressive shift of the brain parenchyma from which the ultrasonic echoes are reflected that effects inclination from vertical of the upright lines of the graphs.

"Velocity" is defined in *Webster's Third New International Dictionary* as 2a (1) time rate of linear motion in a given direction. In the graph of FIG. 8, time is represented by the ordinates. The motion of the brain parenchyma is along a line through the head from the transducer and is either approaching the transducer or receding from the transducer to cause a shift in progressively lower abscissae of the graph representation of which motion produces inclination of the upright lines from vertical.

In the definition of "velocity" quoted above, the same dictionary defines "rate" as 4a quantity, amount or degree of something measured per unit of something else (as time). Thus the "velocity" of the brain parenchyma from which the echoes are reflected is the amount or degree of displacement of such brain parenchyma represented by the successively lower graph abscissae during a unit of time represented by the graph ordinates.

Figure 3:
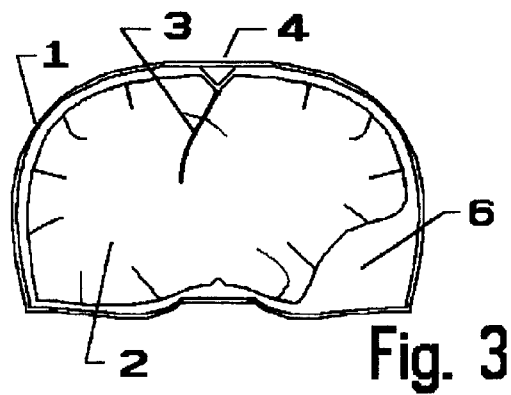
FIG. 3 is a vertical transverse midsection through the head showing an advanced epidural hematoma.

FIG. 7 shows the echo pattern lines as being generally vertical, which would correspond to a brain in normal position within the cranium with no movement of brain relative to the cranium caused by pressure on the brain during the period of time represented by the ordinates. FIG. 8, on the other hand, displays echo patterns corresponding to continuing progressive abnormal movement of the brain relative to the cranium caused by progressively increasing pressure on the brain caused by an expanding hematoma such as shown in FIG. 2 or FIG. 3. The degree of inclination of the upright lines is established by the extent of progressive shift of successively lower abscissae. Such degree of inclination corresponds to the amount of brain movement relative to the cranium. The greater the degree of inclination, the greater is the brain shift.

FIG. 8 represents a typical example in which the duration of the test is ten minutes as indicated by the ordinates. During that time period the rate of displacement or shift of the brain parenchyma relative to the cranium is indicated as 0.05 mm. Combining the time of 10 minutes and rate of brain shift 0.05 mm., the brain has shifted 0.05 mm. in 10 minutes, so the average velocity of the brain shift in 1 hour (60 minutes) is 0.3 mm., which is sufficient to alert medical personnel to monitor a hematoma condition of the patient for an extended period of time up to 24 hours.

In summary the invention provides a method of detecting brain movement relative to the cranium caused by continuing intracranial bleeding, which comprises transmitting a first burst of ultrasound into the head through the cranium along a predetermined path, detecting a first echo pattern composed of ultrasound of the first burst reflected from brain at different depths corresponding to different selected time intervals after transmission of the first burst, after a short delay transmitting a second burst of ultrasound into the head along the same predetermined path as the first burst, detecting a second echo pattern produced by ultrasound of the second burst reflected from brain at the same different depths as used in producing the first burst echo pattern by utilizing the same different time intervals after transmission of the second burst, and comparing any change in depth of the second echo pattern resulting from the second burst with the first echo pattern resulting from the first burst for determining displacement of brain relative to the cranium lengthwise of the ultrasound predetermined path between the first and second bursts.

In a representative operation of the microvelocimeter, the frequency of the ultrasound pulses could be 300 KHz, and the duration of each pulse could be twelve microseconds, with the interval between pulses being one-quarter of a second or one-quarter of a cardiac cycle, so that there would be four transmit-receive cycles emitted and received from each transducer alternately during each second or cardiac cycle. Echoes returning to each transducer are monitored for a period of two hundred microseconds after each pulse is transmitted to obtain ultrasonic echoes from depths up to 15 centimeters. The demodulator 14 demodulates sixteen echo samples spaced at 12.5 microsecond intervals corresponding to a depth of about one centimeter per sample, making a maximum depth of fifteen centimeters. Readouts of six of such samples are shown for each transducer in FIGS. 7 and 8.

Instead of placing transducers to project ultrasonic pulses through the temples, a transducer could be placed to transmit a burst of ultrasound pulses through the foramen magnum as illustrated in FIG. 9. The transducer applied to the foramen magnum will be directed along the vertical axis of the brain for indicating motion of the medulla oblongata, i.e., of the brain stem, relative to the foramen magnum or to the cranium.

FIG. 9 shows the brainstem (medulla oblongata) 18 connected to the spinal cord 21 through the foramen magnum, and the tentorium 20 covering the cerebellum 19. The ultrasound transducer 16 is directing an ultrasound beam through the skin of the back of the neck 17 and through the foramen magnum to the brainstem.

In the claims:

1. In the process of medically examining a person's head by projecting ultrasound into the head, the improvement comprising detecting abnormal very slow progressive brain displacement relative to the cranium over a period of a few minutes caused by continuing intracranial bleeding, by transmitting a series of successive ultrasound bursts separated by short delays into the head for a period of a few minutes, including a first burst of ultrasound into the head along a predetermined path, detecting a first echo pattern composed of ultrasound of the first burst reflected from brain at different depths along such predetermined path corresponding to different selected time intervals after transmission of the first burst, after a short delay transmitting a second burst of ultrasound into the head along the same predetermined path as the first burst, detecting a second echo pattern produced by ultrasound of the second burst reflected from brain at the same different depths along such predetermined path as used in producing the first burst echo pattern by utilizing the same different time intervals after transmission of the second burst as used in detecting the first echo pattern, and comparing the second echo pattern resulting from the second burst with the first echo pattern resulting from the first burst for determining any chance indicating abnormal displacement of brain relative to the cranium lengthwise of the ultrasound predetermined path between the first and second bursts of ultrasound.

2. In the process defined in claim 1, the short delay between the first and second bursts of ultrasound is within the range of 0.25 second to 2.0 seconds.

3. In the process defined in claim 1, synchronizing each burst of ultrasound with the patient's electrocardiogram to differentiate abnormal progressive nonpulsatile brain displacement relative to the cranium from normal swelling and contraction pulsation of the brain during heart systole and diastole.

4. In the process defined in claim 1, each echo pattern includes echoes from brain within the range of four to thirty-two different depths.

5. In the process defined in claim 1, each of the series of bursts of ultrasound produces an echo pattern, and displaying all of the echo patterns of the series simultaneously on a readout.

6. In the process defined in claim 5, displaying in the readout the representation of echoes from different predetermined depths along the predetermined path as abscissae of a graph so that successive abscissae collectively form upright lines.

7. In the process defined in claim 1, the number of ultrasound bursts in the series is selected from the group consisting of 128 bursts, 256 bursts, 512 bursts, and 1024 bursts.

8. In the process defined in claim 1, transmitting the bursts of ultrasound into the head through a location of the cranium selected from the group consisting of the left temporal region, the right temporal region and the foramen magnum region.

9. In the process defined in claim 8 transmitting successive bursts of ultrasound into the head alternately through the left temporal region and through the right temporal region.

10. In the process defined in claim 8 used for quantifying the velocity of brain stem relative to the foramen magnum, transmitting the bursts of ultrasound into the head in the region of the foramen magnum, and comparing the second echo pattern and the first echo pattern for indicating abnormal progressive displacement of the brain stem relative to the foramen magnum caused by continuing intracranial bleeding.

11. In the process defined in claim 1, quantifying velocity of very slow abnormal displacement of the brain relative to the cranium by detecting the echo patterns of the ultrasound bursts, and combining the extent of any brain displacement relative to the cranium during such period of a few minutes with such period of a few minutes to determine the average brain velocity relative to the cranium during a unit of time.

* * * * *

UNITED STATES PATENT AND TRADEMARK OFFICE
CERTIFICATE OF CORRECTION

PATENT NO. : 5,951,476
DATED : September 14, 1999
INVENTOR(S) : K.W. Beach

It is certified that error appears in the above-identified patent and that said Letters Patent is hereby corrected as shown below:

COLUMN   LINE 1        3         before "BACKGROUND OF THE INVENTION" insert paragraph --This invention was made with government support under U.S. Navy Grant No. N00014-96-0630. The government has certain rights in the invention.--

Signed and Sealed this

Twenty-ninth Day of May, 2001

Attest:

NICHOLAS P. GODICI

Attesting Officer          Acting Director of the United States Patent and Trademark Office